US012558141B2

(12) United States Patent
Jacobsen et al.

(10) Patent No.: US 12,558,141 B2
(45) Date of Patent: Feb. 24, 2026

(54) ENERGIZABLE INSTRUMENT ASSEMBLY

(71) Applicant: Medtronic Navigation, Inc., Louisville, CO (US)

(72) Inventors: Brad Jacobsen, Erie, CO (US); Amy Bradley, Westford, MA (US); Xiaoming Cheng, Keller, TX (US); Yeung Chow, Longmont, CO (US); Anjali Dhiman, Commerce City, CO (US); Yahia Laouar, Superior, CO (US); Prakash Manley, Arvada, CO (US); Martin Masson, Keller, TX (US); Molly Ann Megna, Denver, CO (US); Katherine M. Puckett, Denver, CO (US); Wade Schutte, Denver, CO (US); Mohammad Miri, Longmont, CO (US); Juan P. Angulo, Louisville, CO (US)

(73) Assignee: Medtronic Navigation, Inc., Lafayette, CO (US)

( * ) Notice: Subject to any disclaimer, the term of this patent is extended or adjusted under 35 U.S.C. 154(b) by 788 days.

(21) Appl. No.: 17/705,622

(22) Filed: Mar. 28, 2022

(65) Prior Publication Data

US 2022/0313340 A1     Oct. 6, 2022

Related U.S. Application Data

(60) Provisional application No. 63/171,386, filed on Apr. 6, 2021.

(51) Int. Cl.
*A61B 18/14* (2006.01)
*A61B 18/04* (2006.01)
(Continued)

(52) U.S. Cl.
CPC .............. *A61B 18/04* (2013.01); *A61B 34/20* (2016.02); *A61B 2018/00601* (2013.01);
(Continued)

(58) Field of Classification Search
CPC .. A61B 18/04; A61B 34/20; A61B 2034/2065
See application file for complete search history.

(56) References Cited

U.S. PATENT DOCUMENTS 106,825 A     8/1870   Hughes
5,592,939 A   1/1997   Martinelli
(Continued)

FOREIGN PATENT DOCUMENTS

EP     1542600 A2   6/2005

OTHER PUBLICATIONS

International Search Report and Written Opinion regarding Application No. PCT/US2022/023297, mailed Jul. 5, 2022.

*Primary Examiner* — Linda C Dvorak
*Assistant Examiner* — Ryan T Clark

(57) ABSTRACT

A system for altering an energizable instrument for performing a procedure on the subject. The instrument may be tracked during a procedure and a controller may alter operation thereof during the selected procedure. The energizable instrument may have energy provided to a working end to heat a working end to a selected temperature for various procedures such as cutting, coagulation, vaporization, or the like.

21 Claims, 9 Drawing Sheets

(51) Int. Cl.
　　*A61B 34/20*　　　　(2016.01)
　　*A61B 18/00*　　　　(2006.01)

(52) U.S. Cl.
　　CPC ............... *A61B 2018/00708* (2013.01); *A61B 2018/00726* (2013.01); *A61B 2018/00767* (2013.01); *A61B 2034/2065* (2016.02); *A61B 2034/2074* (2016.02)

(56) References Cited

U.S. PATENT DOCUMENTS

| | | | |
|---|---|---|---|
| 5,772,594 A | 6/1998 | Barrick | |
| 5,913,820 A | 6/1999 | Bladen et al. | |
| 5,983,126 A | 11/1999 | Wittkampf | |
| 6,940,941 B2 | 9/2005 | Gregerson et al. | |
| 7,001,045 B2 | 2/2006 | Gregerson et al. | |
| 7,001,391 B2 | 2/2006 | Estes et al. | |
| 7,011,661 B2 | 3/2006 | Riedel et al. | |
| 7,106,825 B2 | 9/2006 | Gregerson et al. | |
| 7,108,421 B2 | 9/2006 | Gregerson et al. | |
| 7,188,998 B2 | 3/2007 | Gregerson et al. | |
| 7,697,972 B2 | 4/2010 | Verard et al. | |
| 7,751,865 B2 | 7/2010 | Jascob et al. | |
| 8,238,631 B2 | 8/2012 | Hartmann et al. | |
| RE44,305 E | 6/2013 | Foley et al. | |
| 8,644,907 B2 | 2/2014 | Hartmann et al. | |
| 8,842,893 B2 | 9/2014 | Teichman et al. | |
| 9,737,235 B2 | 8/2017 | Hartmann | |
| 2004/0097948 A1* | 5/2004 | Heldreth | A61B 34/20 606/80 |
| 2004/0199072 A1 | 10/2004 | Sprouse et al. | |
| 2016/0331473 A1 | 11/2016 | Yamamura | |
| 2019/0365477 A1 | 12/2019 | Reddy et al. | |
| 2020/0237445 A1 | 7/2020 | Snyder et al. | |

* cited by examiner

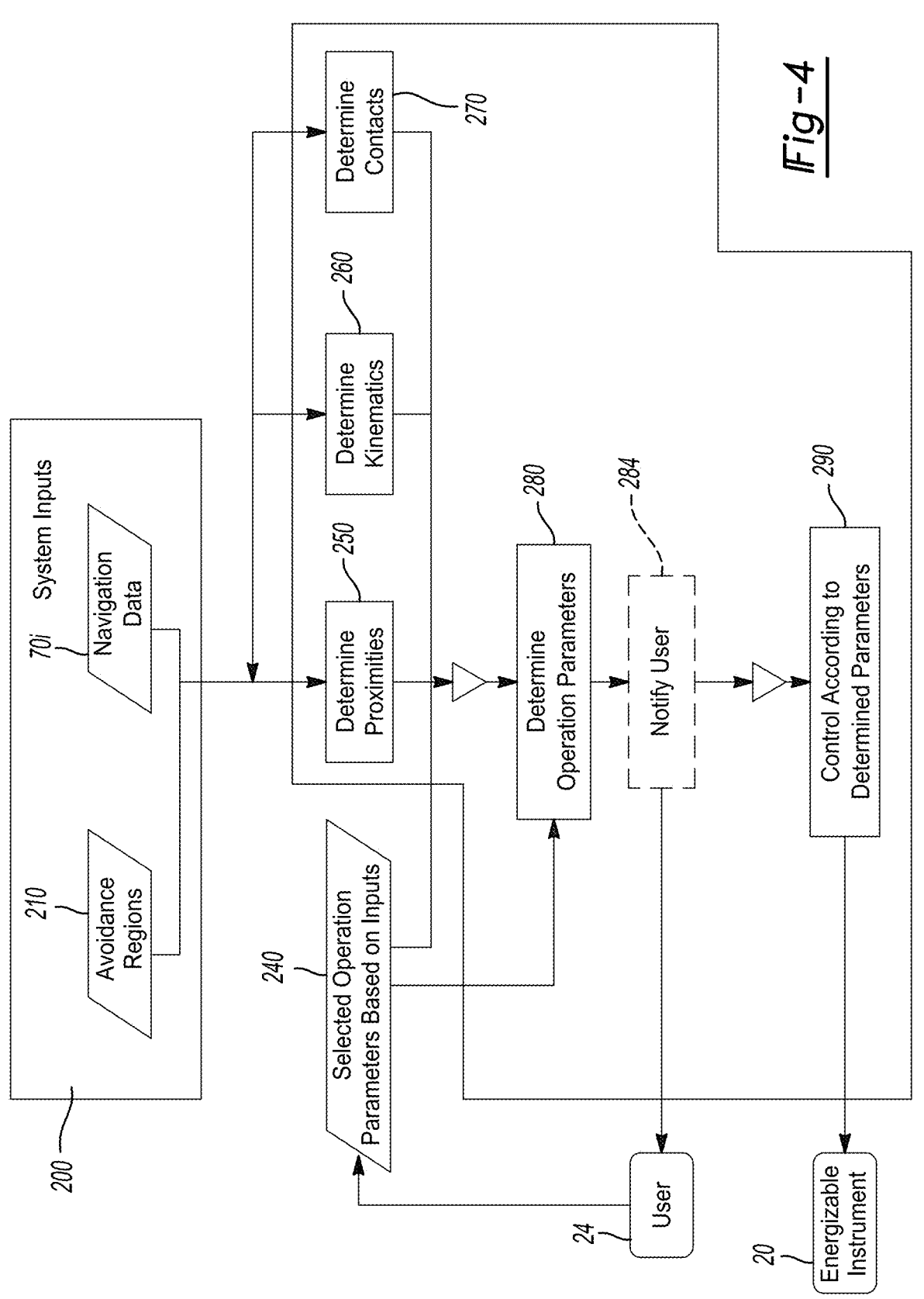
_Fig-4_

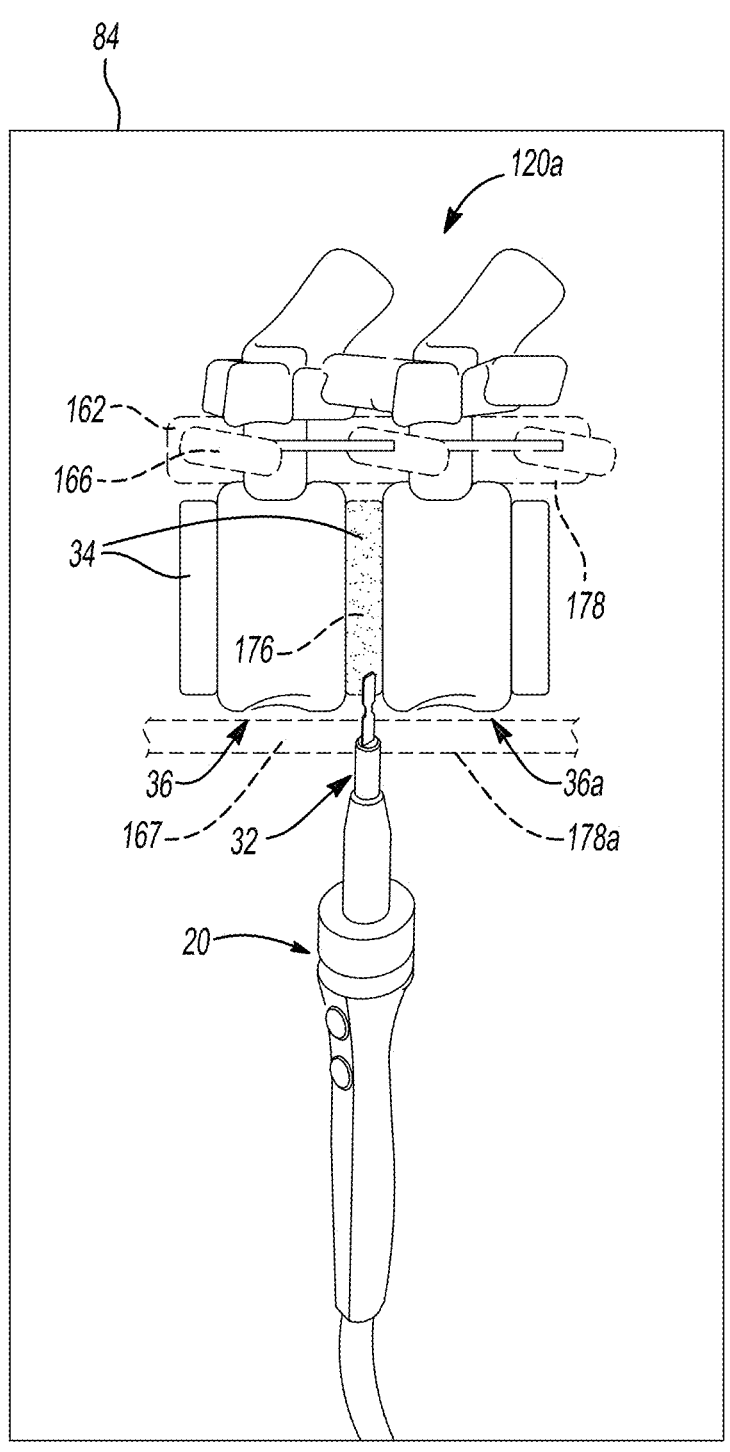
_Fig-6B_

ENERGIZABLE INSTRUMENT ASSEMBLY

CROSS-REFERENCE TO RELATED APPLICATIONS

This application claims the benefit of U.S. Provisional Application No. 63/171,386 filed Apr. 6, 2021. The entire disclosure of which is incorporated by reference.

FIELD

The present disclosure relates to a powered instrument, and particularly to a powered instrument assembly with selected feedback.

BACKGROUND

During selected procedures, an instrument may be powered and operated, particularly a working end thereof. For example, the tool may be energized for performing a procedure. Instruments may include energized instruments that may be used to cut or resect selected material. The instrument may be an effective cutting instrument that may reduce various intrinsic mechanical feedback.

During a selected procedure, such as a surgical procedure, the user (e.g. a surgeon) of the instrument may need to rely solely on visual cues and experience for determining a location of the working end or tip. During a procedure, at least a working end may be hidden from direct view or complete direct view of the user. Thus, an open experience may be required to properly perform a procedure.

SUMMARY

This section provides a general summary of the disclosure, and is not a comprehensive disclosure of its full scope or all of its features.

During and/or prior to a procedure to a subject, the subject may have a predefined location or portion for having a procedure performed thereon. For example, a skull of a patient may be selected to have a burr hole formed therein. The location, size, etc. of the burr hole may be predefined during a planning procedure. The selected procedure area or volume, however, may also be selected during a procedure. The energizable or powered instrument may also be operated to perform other procedures. In various embodiments, the energizable or powered instrument may be an electrosurgical instrument. For example, the energizable instrument or may be operated to perform a spinal procedure. In various embodiments, vertebra resection for fusion and/or disc replacements may be operated. Instruments for such procedures include one or more of a PLASMABLADE® Precise Soft Tissue Dissection Devices, including the various PlasmaBlade® X, PlasmaBlade® ENT, PlasmaBlade® PLUS, and/or PlasmaBlade® Needle Dissection Devices, sold by Medtronic, Inc. having a place of business in Minnesota and/or Medtronic Advanced Energy LLC. having a place of business in Louisville, Colo.

A navigation system may track the instrument and a control or power system that may be altered during its use to change a parameter, such as a cutting speed, power, duty cycle. The operation of the instrument may be altered based on a tracked position and orientation, or a combination of both that may be referred to as pose of the instrument.

Further areas of applicability will become apparent from the description provided herein. The description and specific examples in this summary are intended for purposes of illustration only and are not intended to limit the scope of the present disclosure.

DRAWINGS

The drawings described herein are for illustrative purposes only of selected embodiments and not all possible implementations, and are not intended to limit the scope of the present disclosure.

FIG. 4 is a schematic view of system and selected inputs and outputs, according to various embodiments;

FIGS. 6A through 6D are displayed views of an operation of a system during a procedure, according to various embodiments.

Corresponding reference numerals indicate corresponding parts throughout the several views of the drawings.

DETAILED DESCRIPTION

Example embodiments will now be described more fully with reference to the accompanying drawings.

Figure 1:
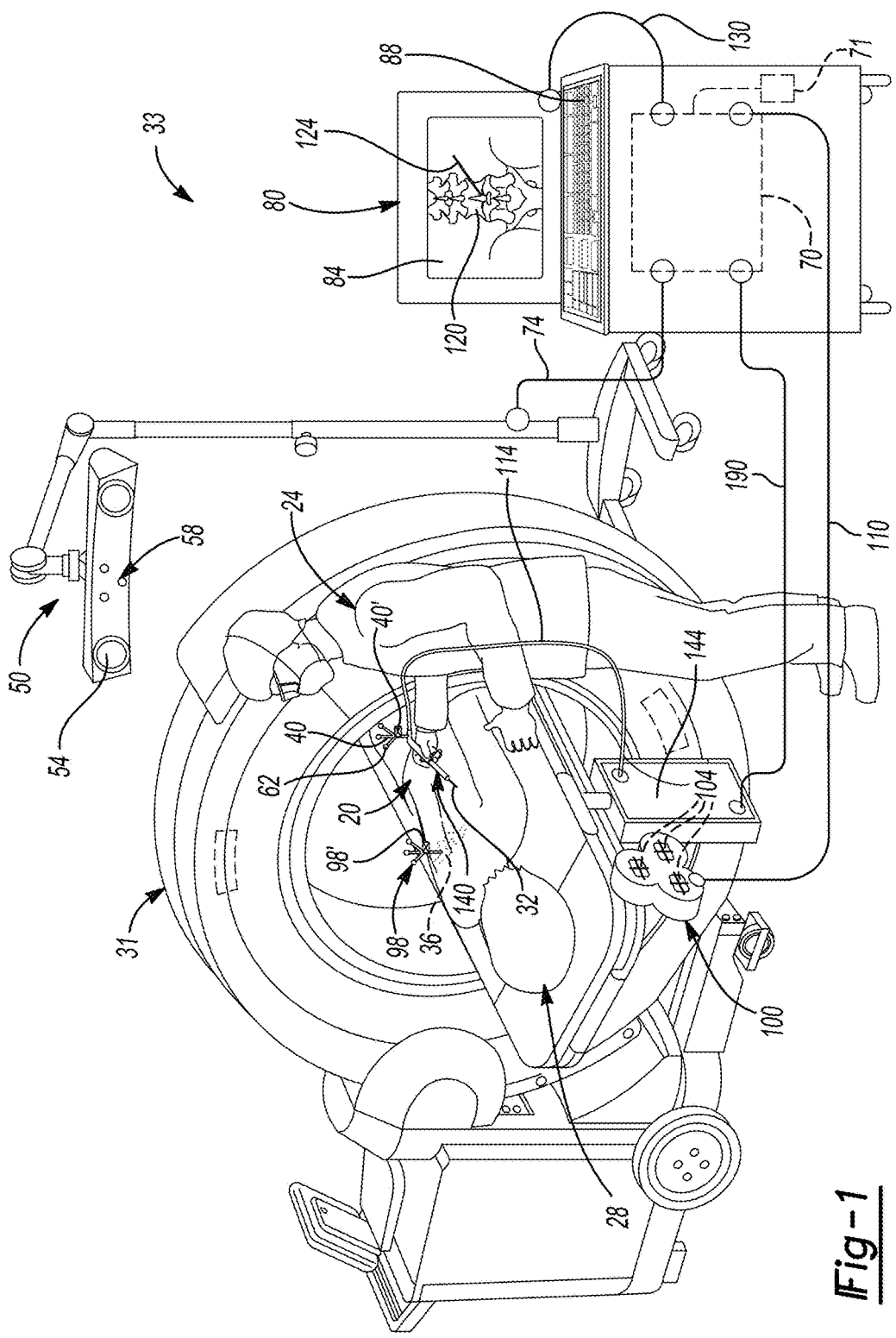
FIG. 1 is an environment view of a tracked instrument assembly.

FIG. 1 is an environmental view of an instrument, such as an energizable instrument 20, being used by a user 24, to perform a procedure on a subject (e.g. a patient) 28. The energizable instrument 20 may be an electrosurgical instrument including an RF instrument. The instrument 20 may energize a tip or working end 32 of the instrument 20. Thus, the instrument may also be referred to and understood to be an instrument that is able to be energized and referred to as an energizable instrument 20.

In various embodiments, the energizable instrument 20 may include the working end 32 for performing a select procedure, such as forming or resecting tissue, such as relative to a spinal column, including a spinal disc 34 relative to a vertebra 36, or other selected procedure. It is understood, however, that the energizable instrument 20 may be used for performing other procedures such as a removal of material relative to and/or in the vertebrae.

For example, the energizable instrument 20 may be operated to remove a portion of a vertebra in a selected procedure, including a laminectomy procedure or other appropriate spinal procedure. In addition, and or alternatively thereto, the working end 32 may be used to remove soft tissue such as the disc 34 as a discectomy. Further, it is understood that the energizable instrument 20 may be used to perform a procedure on a non-living subject such as to form a hole in an airframe, an automotive frame, or the like. Accordingly, the energizable instrument 20 is not required to be used with a living subject, such as a human patient.

The energizable instrument 20 may include a portion, such as a member, that is tracked and/or navigated relative to the subject 28 with various systems and/or procedures. For example, a tracking system, as discussed further herein, may include a tracking device 40 that may be connected to the energizable instrument 20 to track a location of the energizable instrument 20, including the working end 32, relative to the subject 28, such as the vertebra 36. It is understood by one skilled in the art that the tracking device, such as the tracking device 40, may be positioned away from the working end 32 when the working end is generally fixed or at a known pose relative to the tracking device 40. In addition or alternatively, a tracking device 40a (FIG. 2) may be positioned at or adjacent to the working end 32. Appropriate tracking systems include those disclosed in U.S. Pat. Nos. 8,842,893 and/or 8,644,907, both incorporated herein by reference. It is understood that image data may be acquired of the subject 28 to create images, as discussed herein. To acquire the image data, an imaging system 31 may be used prior to beginning a procedure or after a procedure has begun, the procedure may include operation of the energizable instrument 20. The imaging system 31 may include an O-arm® imaging system sold by Medtronic, Inc. and/or may include those disclosed in U.S. Pat. Nos. 7,188,998; 7,108,421; 7,106,825; 7,001,045; and 6,940,941; all of which are incorporated herein by reference. The imaging system, such as the O-arm® imaging system may include a generally or substantially O-shaped gantry. The gantry may define or form an internal volume from the annular shape of the gantry. The image collection portions, such as a detector and source, may be enclosed by and/or move within the annular volume of the gantry. Other possible imaging systems can include C-arm fluoroscopic imaging systems which can also generate three-dimensional views of the patient 28.

The tracking system may be a part of a navigation system 33 to assist in performing selected procedures, such as a surgical procedure on the subject 28, and may include those as generally known in the art. For example, navigation systems may include those as disclosed in U.S. Pat. Nos. 5,772,594; 5,913,820; 5,592,939; 5,983,126; 7,751,865; and 8,842,893; and 9,737,235 and those disclosed in U.S. Pat. App. Pub. No. 2004/0199072, all incorporated herein by reference. Tracked poses may be displayed on images or relative to images due to registration of a location of a subject or real space to an image space, also as disclosed in the U.S. patents and publications as incorporated above. Further, tracking systems may include the Stealth Station® 58® tracking system, and AxiEM™ tracking system, all sold by Medtronic Navigation, Inc.

The tracking systems may include various features such as an optical tracking systems, electromagnetic (EM) tracking systems, ultrasonic tracking systems, or the like. As illustrated above, the instrument may be tracked with one or more tracking system, such as by registration between the tracking systems and/or co-registration, as disclosed in U.S. Pat. App. Pub. No. 2020/0237445, incorporated herein by reference. Nevertheless, as illustrated in FIG. 1, for example, a tracking system may include one or more localizers that may include portions that include cameras and/or antennas for receiving/and or transmitting a signal for tracking. Localizers may include an optical localizer 50 that includes one or more cameras 54 that may detect or "view" a tracking device 40 connected to the energizable instrument 20. The localizer 50 including the cameras 54 may emit a selected radiation, such as infrared radiation from emitters 58, that is reflected by one or more trackable portions 62 that are associated with the tracking device 40. The trackable portions 62 may be viewed by the cameras 54 and a signal may be transmitted to a navigation processor unit 70. The navigation processor unit 70 may include various features, such as a navigation probe interface (NPI), as discussed further herein. The navigation processor unit 70 may also include a coil array controller (CAC) for various types of tracking systems. Various features such as the NPI, the CAC, or other portions may be provided as separate units from the navigation processor unit 70 or separate modules for interacting with various portions of the navigation system, as is generally known in the art. Further, the processor system 70 may interact with a memory system 71 that may include selected instructions and/or predetermined parameters that may be recalled by the processor 70. The memory 71 may be local or remotely accessed and any appropriate type of memory, including non-transitory and physical memory.

Nevertheless, the localizer 50 may communicate with the navigation processor unit 70 via a selected communication portion 74. The communication portion 74 may be a wired or a wireless communication with the navigation processor unit 70. The navigation processor unit 70 may communicate with a selected system, such as a workstation, a terminal, or the like that includes a display system or display module 80 having a display screen 84 and one or more user inputs 88. It is understood, however, that the display 84 may be separated for the processor unit 70 and/or in addition thereto, such as a projected display, a headset display (e.g., augmented reality systems). The user inputs 88 may include a keyboard, a mouse, a touch screen, or other tactical input. Further inputs may also include a foot switch, verbal inputs, visual inputs, or the like.

A subject tracking device 98 may also be connected, such as fixed, relative to the subject 28. In various embodiments, the subject tracking device 96 may be fixed to a vertebra 36. In various embodiments, the subject tracking device 98 may, however, be connected relative to the subject 28. Generally, the subject tracking device is fixed relative to a selected portion of the subject 28.

In various embodiments, alternative or additional tracking systems may be provided, such as an electromagnetic tracking systems including an electromagnetic tracking array, such as a coil array 100. The coil array 100 may include one or more coil elements 104 that emit and/or receive an electromagnetic signal from an electromagnetic (EM) tracking devices, such as the subject tracking device 98' associated and/or connected to the patient 28 or a tracking device 40' and/or tracking device 40a connected to the energizable instrument 20. The coil array 100 may communicate with navigation processing unit 70 via a communication portion 110 similar to the communication portion 74 from the localizer device 50 to the navigation processing unit 70. Further, each of the tracking devices may communicate with the navigation processing unit 70 via selected communication lines such as communication portion 114 so that a pose of the selected tracking devices, including tracking device 40 and tracking device 98 may be determined with a navigation processing unit 70 is used to generate navigation data to determine a pose of the related portion, such as the instrument. It is understood that one or more than one tracking system may be used simultaneously and/or serially during the selected procedure. Any of the communication portions may be wired, wireless, and/or combinations thereof.

The display screen 84 may display an image 120 of a portion of the subject 28, such as an image of the disc 34 and/or vertebra 36. The image 120 may be based on or generated with image data acquired with the imaging system 31 as discussed above. Displayed relative to the image 120 and/or superimposed on the image 120 of the patient 28 may be a graphical representation, also referred to as an icon, 124. The icon 124 may represent a position and orientation, such as a pose, of the energizable instrument 20 that may include the tool 32, relative to the subject 28. The represented pose may also be of only a portion of the assembly 20. The pose of the energizable instrument 20, or a portion thereof, relative to the subject 28 may be determined by registering the energizable instrument 20 relative to the subject 28 and thereafter tracking the location of the energizable instrument 20 relative to the subject 28.

Registration may include various techniques, such as those disclosed in U.S. Pat. Nos. RE44,305; 7,697,972; 8,644,907; 8,238,631; and 8,842,893; and U.S. Pat. App. Pub. No. 2004/0199072, all incorporated herein by reference. Generally, registration includes a mapping (i.e., transformation) between the subject space defined by the subject 28 and the image space defined by the image 120. This may be done by identifying points in the subject space (i.e. fiducial portions) and identifying the same points in the image space (i.e. image fiducials). A map of the image space to the subject space may then be made, such as by the navigation system. For example, points may be identified manually, automatically, or a combination thereof in the image data, such as in the image 120.

Related points may be identified in a subject space, such as defined by the subject 28. For example, the user 24 may identify a spinous process in the image 120 and an instrument tracked by one or more of the tracking systems, including the localizers 50, 100, may be used to identify a spinous process at the vertebrae 36. Once an appropriate number of points are identified in both the image space of the image 120 and the subject space of the subject 28, a map may be made between the two spaces. The map allows for a registration between the subject space defined by the subject, also referred to as a navigation space, and the image space defined by the image 120. Therefore, the instrument, or any appropriate portion, may be tracked with a selected tracking system and a poise of the instrument may be identified or represented relative to the image 120 with the graphical representation 124.

In various embodiments, registration may be substantially automatic. For example, when the imager 31 is tracked while acquiring images of the subject 28, such as a tracked O-Arm® imager, registration is automatic. Here the image space is characterized with respect to the imager tracker and the imager tracker is tracked in the same space as the patient tracker 98 so that patient images register automatically to the patient tracker. In a further example, when using an imageable patient tracker, such as an automatic intraoperative registration frame, registration is also automatic. Here the image contains known features of the imageable patient tracker so that patient images register automatically to the patient tracker.

As discussed above, registration of the energizable instrument 20 relative to the subject 28, such as with or to the subject tracking device 98, may be made at a selected point in a procedure. The image 120 may then be displayed on the display screen 84 and a tracked location of the energizable instrument 20 may be displayed as the icon 124 relative to the image 120. The icon 124 may be superimposed on the image 120 to display a pose of at least a selected portion of the energizable instrument 20, such as the working end 32 of the energizable instrument 20. The pose may include a location that includes three degrees of freedom in space (for example, including at least one of a XYZ position) and a selected number (e.g., three) degrees of freedom orientation information location (for example, including at least one of yaw, pitch and roll orientation). The pose may be determined and/or calculated by the navigation processing unit 70 and communicated to the display device 80 via a selected communication line, such as communication portion 130. The communication portion 130 may be a wired or wireless or other appropriate communication portion. Further, it is understood that the navigation processor unit 70 may include various features such as a selected processor (e.g., an application specific integrated circuit (ASIC), general purpose processor or the like). The navigation processor unit 70 may also include the memory system 71 (e.g., non-transitory memory systems including spinning hard disks, non-volatile solid state memory, etc.) that includes selected instructions, such as those to perform the tracking, registration, superimposing of the icon 124 on the image 120, or the like. Therefore, the determined pose of the energizable instrument 20 (for example the selected portion of the energizable instrument 20, as discussed further herein), may be displayed relative to the subject 28 by the icon 124 relative to the image 120. The user 24 may then be able to view the display screen 84 to view and/or comprehend the specific pose of the selected portion of the energizable instrument 20 relative to the subject 28 by viewing the display 84.

Figure 2:
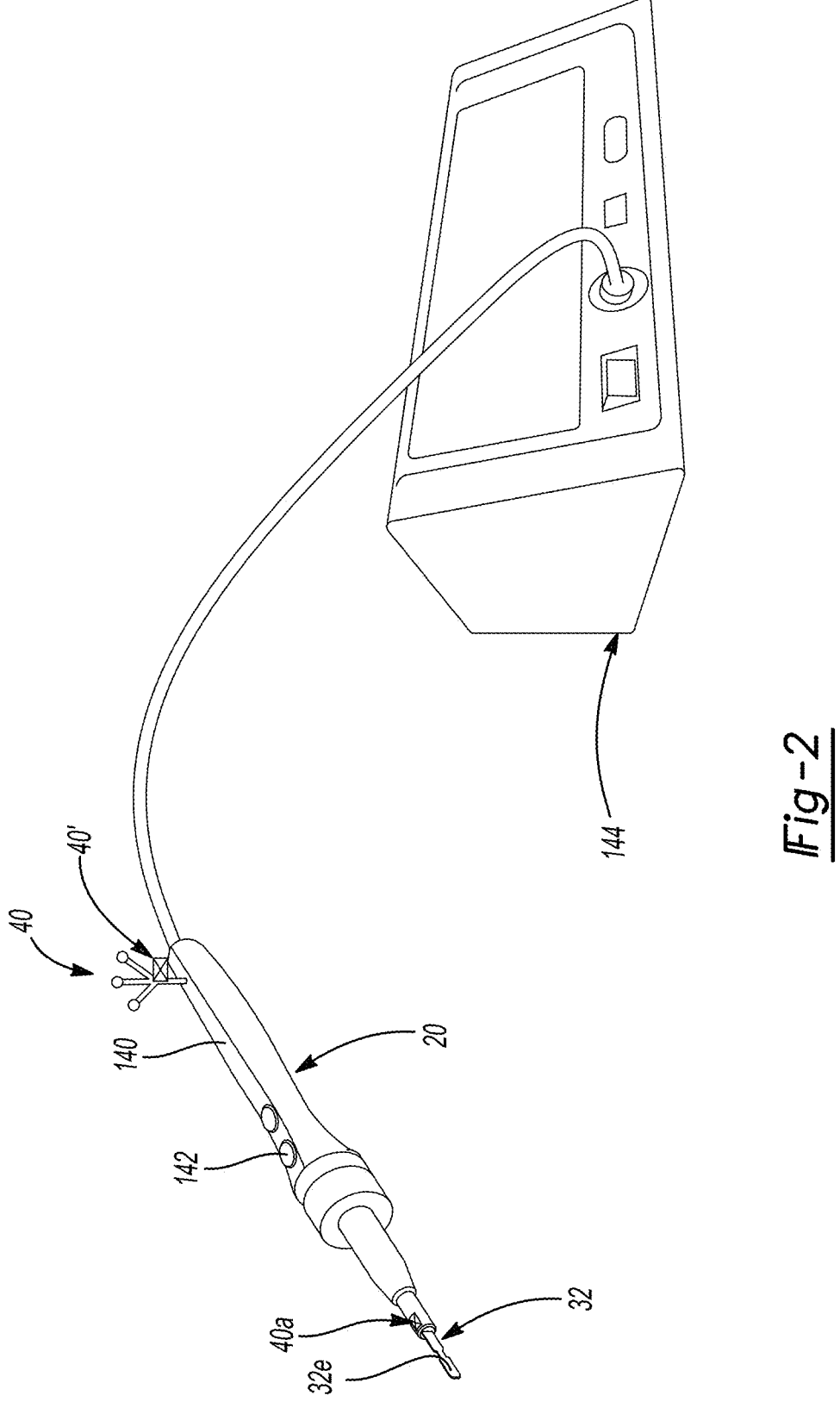
FIG. 2 is a schematic illustrated of a energizable instrument and controller, according to various embodiments.

In various embodiments, the energizable instrument 20 may include various components which may include a housing 140. The housing 140 may be grasped by the user 24 to move and/or manipulate the working end 32. The housing 140 may also include selected controls to operate the energizable instrument 20. The energizable instrument 20 instrument 20 may include the various PLASMABLADE® Dissection Devices, as noted above. The working end 32 of the energizable instrument 20 instrument 20 may be operated according to selected parameters to generate an energized region or portion generally at an edge or portion 32e of the working end 32. For example, as illustrated in FIG. 2, the edge 32e of the working end 32 may be energized. The energy may be provided due to a selected frequency, amplitude, duty cycle, amperage, power, voltage, etc. that may be provided from a generator 144. The generator 144 may also be referred to as a controller that controls operation including the power generated and delivered to the instrument 20. The controller 144 may be operated, at least in part, by the controls 142 included on the housing 140. The controller 144 may be any appropriate controller 144 such as the AEX™ generator provided with the PLASMABLADE® Precise Soft Tissue Dissection Devices, sold by Medtronic, Inc.

Figure 3:
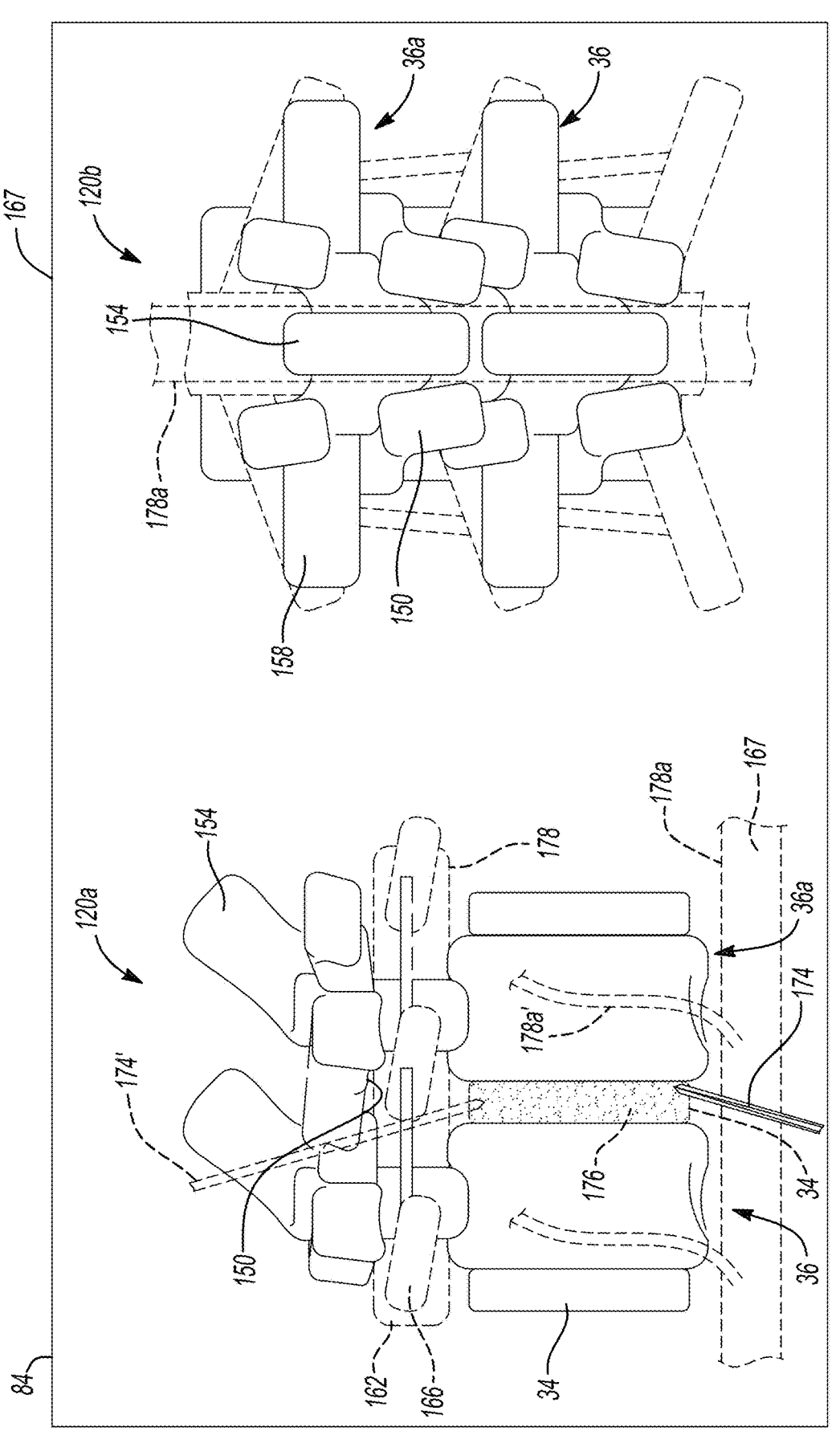
FIG. 3 is a schematic illustration of a portion of a spinal column from two directions.

As discussed above, a procedure may be performed on a subject 28. The procedure performed on the subject 28 may be performed with the energizable instrument 20 having the working end 32. The energizable instrument 20, as discussed above, may be navigated relative to the subject 28. In various embodiments, image guided procedures or image guided navigation may occur. Accordingly, the image 120 on the display screen 84 may include imaged portions of the subject 28. For example, as illustrated in FIG. 3 a medial-to-lateral (ML) (or vice versa) image portion 120a and an anterior-to-posterior (AP) (or vice versa) image view 120b that may be illustrated on the display screen 84 as the image 120. The image 120, therefore, may include various portions, such as a first or ML view 120a and a second or AP view 120b. It is understood, however, that additional views or images may also be viewed for various purposes such as inferior to superior, or selected angles relative thereto.

In various embodiments, a portion of the image may be segmented for various purposes, such as planning a selected procedure. As discussed above, the working end 32 may be for performing a procedure on the subject 28, such as a discectomy, spinal decompression, inter-vertebral body fusion, or other selected procedures. A procedure may include moving the working end 32 to remove a selected portion of the subject 28, such as a selected portion of the anatomy of the disc 34 between one or more vertebra 36.

The vertebrae 36 may include the first vertebrae 36 and a second vertebrae 36a, as illustrated in FIG. 3. The vertebrae may include various portions such as facets 150 or edges thereof, including a spinous processes 154. The vertebrae 36 may include portions that are included on each vertebrae such as the facet 150, the spinous process 154, and a transverse processes 158.

The disc 34 may be injured and/or require repair. In various embodiments, at least a portion of the disc 34 may be removed and/or removed and replaced. Thus, at least a portion of the disc 34 may be cut with the working end 32. Near or adjacent the vertebrae 36 and/or the disc 34 may be non-bony tissue and/or non-disc tissue and may include other soft tissue, such as nerve tissue. For example, a spinal cord 162 of the subject may extend through the plurality of vertebrae 36. Further, various nerves or nerve roots 166 may extend from the spinal cord 162. The spinal cord 162, and the various nerve portions thereof, may generally be selected to not be resected or otherwise affected during a selected procedure. Other soft tissues may include blood vessels 167, including the aorta and/or various arteries.

The image 120 may be segmented to segment various portions such as the vertebrae portions 36, one or more of the discs 34, the blood vessels 167, the spinal cord 162, and/or the nerve roots 166. For example, as illustrated in FIG. 3, the disc 34 may be segmented and a graphical representation thereof may be displayed, such as illustrating the segmented region with large dashes, a selected color, lines or dashes with a blink rate, etc. The soft tissue or any appropriate portion, including the spinal cord 162, may be segmented and illustrated with dashes, selected color, etc. It is understood that any appropriate identification may be made such as color, line weight, or the like. It is further understood that specific visual representations of the segmentation need not be made.

Segmentation of the image 120 may be formed in any appropriate manner, such as automatically, manually, or with manual input and automatic thereafter. For example, the user 24 may select an area or region (e.g. a pixel, a voxel, an area, etc.) and the system, such as the navigation processor 70, may execute selected instructions to segment the image 120. It is understood that a processing unit of any appropriate type may be used in addition to or in combination with a navigation processing unit 70. Therefore, various imaging processing, such as segmentation, need not be performed with the navigation processing unit 70. It is understood, however, that the processing units may be generally general processors and able to execute selected instructions for performing various tasks from a storage medium, such as the memory 71.

The image 120, whether segmented or not, may also be used to identify the plan for performing a procedure. The plan can be saved and recalled for performing a procedure. Generally, the plan may include various features or portions such as a plan region or volume. The plan may include a trajectory, volume, or other portion that may be resected with the working end 32. Further, the plan may include a path to achieve the selected resection and/or the amount of resection. The plan may also include areas that are to be avoided or cautioned. For example, the spinal cord 162 may be identified as an area or region not to be contacted, penetrated, or accessed with the working end 32. For example, the plan may include a trajectory or path representation 174, region to be resected 176, and avoidance regions 178, 178a, 178a'. Each may be illustrated with an appropriate graphical representation, such as a color, icon, etc. It is understood that the trajectory path may be from any selected or appropriate pose or direction, such as anterior as illustrated in FIG. 3 by the path 174 and/or posterior path 174'. The avoidance regions 178, 178a, 178a' may be any appropriate portions or regions such as nerves, including the spinal cord 162 and/or blood vessels 167.

The system, such as including the navigation processor 70, may automatically identify selected regions to be identified as avoided regions or volumes. A selected avoidance region may include the spinal cord 162. Accordingly, the system may automatically segment and identify the spinal cord 162. Further, however, in addition or alternatively thereto, the user 24 may identify regions that are segmented in the image 120. Also, various regions to be avoided may be identified in the image 120 and saved for later access, such as during the procedure of moving the working end 32 relative to the subject 28.

In or with the image, regions to be avoided and/or regions for performing a procedure may be identified in the subject 28. The region to be avoided may be identified with a first instrument that is tracked. For example, a tracked/navigated pointer probe may be tracked to identify a volume in the subject space of the subject 28, such as relative to the vertebrae 36. The user 24 may move the tracked instrument to identify a region to be avoided and/or region to be operated on or for a procedure to be performed at a first time. Again, these regions may then be saved and recalled at a second time, such as after saving them, and during a procedure for providing selected feedback to the user 24.

Accordingly, during a selected procedure, the system, such as the navigation system, may be used to determine or provide feedback to the user 24 of the pose of the tool 32 relative to selected predefined or saved regions, such as regions or volumes to be avoided. Further, the controller 144 for the energizable instrument 20 may also provide selected feedback and/or receive signals from the energizable instrument 20 and provide feedback based upon the saved and identified region that may be identified in the image 120 and/or in the subject 28, as discussed above. Further, the saved regions may be saved in a selected memory system, such as the memory 71 included with the navigation processing unit 70. The controller 144 of the energizable instrument 20 may communicate with the processing unit 70, via a select communication line, such as the communication portion 190. As discussed above, the communication portion 190 may be any appropriate type such as a wired, wireless, or a combination thereof communication channel. Accordingly, the navigation processing unit 70 may communicate with the controller 144 for providing signals regarding the tracked or navigated pose of the energizable instrument 20 and/or signals from sensors associated with the energizable instrument 20.

With continuing reference to FIG. 1 and additional reference to FIG. 4, the instrument assembly 20 may be controlled by the controller 144 and/or other appropriate control system, as discussed above. The controller 144 may include a processor module that may receive various inputs, such as inputs 200. The inputs 200 may be processed according to selected instructions, as discussed further herein, to provide selected outputs to the user 24 and/or for operation of the energizable instrument 20 and particularly to powering or operating the working end 32. It is understood, however, that any appropriate processor may receive the selected inputs 200 and make the selected determination, as noted herein, to generate the appropriate outputs as also discussed herein. For example, the navigation processor 70 or other appropriate processor.

The energizable instrument 20 may be operated for removing selected portions of tissue. As discussed above, the controller 144 may operate to generate power that is transmitted to the working end 32. The working end may then energize the edge 32e to aid tissue resection. In various embodiments, varying power may be provided by the controller that may also include a generator 144 to the working end 32 to achieve different or varying energies at the edge 32e. The working end 32, therefore, may be used to cut and/or coagulate selected tissue. The energizable instrument 20 may be used for selected procedures and the following discussion regarding cutting or removing a portion of the disc 34 is merely exemplary and includes the energizable instrument 20 controlled by the controller 144 that may be in communication with the navigation processing unit 70 of the navigation system 33.

Generally, as discussed above, selected inputs may be provided to the controller 144. As also discussed above, the controller 144 may include a selected processor and/or controls to control the operation of the energizable instrument 20. It is understood, however, that the navigation processing unit 70 may also be used to control the energizable instrument 20 and the controller 144 may simply allow for communication of the selected inputs and/or outputs to the energizable instrument 20. Nevertheless, the inputs 200 may provide input to the controller 144 to control the energizable instrument 20.

The identified regions or areas or volumes to be avoided, as discussed above, may be identified as avoidance regions or zones or areas or volumes 210, these may include spaces, volumes, portions, etc. The avoidance regions 210 may also include caution zones. For example, an avoidance region may include a determined or segmented boundary of the spinal cord 162 and a caution zone may be a distance therefrom, such as 1 millimeters (mm), including about 0.5 mm to about 2 mm, etc. The avoidance spaces may be saved and recalled, such as with the navigation processing unit 70. The avoidance regions 210 and other zones, such as caution zones, may be provided to the controller 144 for controlling the energizable instrument 20.

The avoidance spaces or caution zone may be selected or determined to have selected distances that may vary depending upon an approach direction and/or pose of an instrument during or at the approach. For example, an anterior approach to an anatomical feature may include a 1 mm avoidance space while a posterior approach may include a 3 mm avoidance space. Thus, an avoidance space relative to a feature may vary depending upon a direction of an approach thereto. The direction and/or pose of the approach of an instrument may be determined with the navigation, as discussed herein.

During a selected procedure, tracking or navigation data 70i from the navigation processing unit 70 may also be input with or to the controller 144. The navigation data can include the determination of a pose of the energizable instrument 20 and/or the working end 32 and/or the edge 32e. As noted above, the pose of the energizable instrument 20 and/or the working end 32 may be determined relative to the image 120 and/or the subject 28 sue to the registration between the two. Thus, the pose of the working end 32 relative to the various input zones may be known and/or displayed with the display 84.

All of the input information 200 may be provided to the controller 144. Further, the user 24 may input various operation parameters 240. The selected operation parameters 240 may include parameters such as selected feedback to the user 24, operation of the energizable instrument 20, or other appropriate feedback or notifications of the user 24. Further, the operation parameters 240 may include a distance from the avoidance regions 210 to provide feedback and/or other operation of the energizable instrument 20.

The controller 144 based upon the inputs 200 and the operation parameters 240 may make selected determinations and/or feedback or controls. Generally, the controller 144, may make a determination of proximities to selected regions, such as the avoidance regions, at block 250, a determination of kinematics of the energizable instrument 20 and/or the working end 32 at block 260, and a determination of contacts in block 270. The determination of proximities 250 may be based upon selected information, such as the navigation information or inputs 70i from the tracking system including the navigation assembly or processing unit 70. As noted above, the navigation system 33 may determine the pose of the energizable instrument 20 relative to the selected regions. Thus, the navigation system 33 may output a distance of the energizable instrument 20 from selected regions that may be used to determination of operation of the energizable instrument 20 by the controller 144.

The determination of kinematics (also referred to as a kinematic feature) in block 260 may also be based at least in part on the navigation data 70i, that may be used to determine speed, direction, etc. of movement of the energizable instrument 20 and/or the working end 32. The kinematics may include a determination of a rate of movement and/or a type of movement. For example, a speed of movement along the path 174 and/or within the region to be cut, such as the disc 34.

Further, the determination of contacts in block 270 may be determining whether the working ends 32, is contacting selected portions of the anatomy including selected bony portions. The determination may be based on the tracked pose of the energizable instrument 20 and/or the working end 32. The navigation system 33, as discussed above may track the energizable instrument 20 and determine the pose relative to the subject 28, such as via the image 120. Thus, a determination of contact of the energizable instrument 20 and/or the working end 32 may be based on the navigation data 70i from the navigation system 33.

The determinations by the controller 144, such as by executing instructions with a processor, may further include determining the energizable instrument parameters in block 280. The determination of the energizable instrument parameters in block 280 may include selected operation parameters of the energizable instrument 20, as discussed further herein. The determined energizable instrument parameters in block 280 may then be used to optionally notify the user 24 in block 284. Notification of the user 24 in block 284 may include a visual indication on the display screen 84, an audio or audible signal, or other appropriate feedback. Accordingly, the user 24 may be provided feedback separate from the energizable instrument 20, such as with the display screen 84.

The controller 144 may control the energizable instrument 20 in an appropriate manner. For example, as discussed above, the controller 144 may be generate a control signal and/or power for energizing the energizable instrument 20. The controller 144 may include a generator to generate a power signal that is transmitted to the energizable instrument 20 and the working end 32. The controller 144 may further generate a control signal that controls the generator, as discussed herein.

The energizable instrument 20 may be energized with the power signal at a selected frequency, amplitude, power, voltage, and/or duty cycle to achieve a selected power at the working end 32. For example, the controller 144 may generate a power of about 0.5 watts (W) to about 100 W, including about to about 50 W and further including about 2 W, about 5 W, or any other appropriate power. The controller 144, therefore, may control the energizable instrument 20 based upon the parameter inputs as discussed above. The operation of the energizable instrument 20 may vary based upon the inputs and a selected operation of the energizable instrument 20. As discussed further herein, the energizable instrument 20 may be selected to have a greater power further form the avoidance areas or regions and a lower power near the avoidance areas or regions. Thus, the controller 144 may control the power provided to the energizable instrument 20 to alter an operation at the working end 32. Thus the controller 144 may be provide outputs for direct feedback to the user 24 and/or alter an operation of the energizable instrument 20, as discussed further herein.

The controller, including the controller 144, may receive various inputs 200 and those from the user 24 in block 240. With continuing reference to FIGS. 1-4, and with further reference to FIG. 5, operation of the energizable instrument 20 will be discussed. It is understood that the discussion herein is according to various embodiments, and that various disclosed features and inputs may be used in appropriate combination and/or without selected inputs, for operation of the energizable instrument 20.

Figure 5:
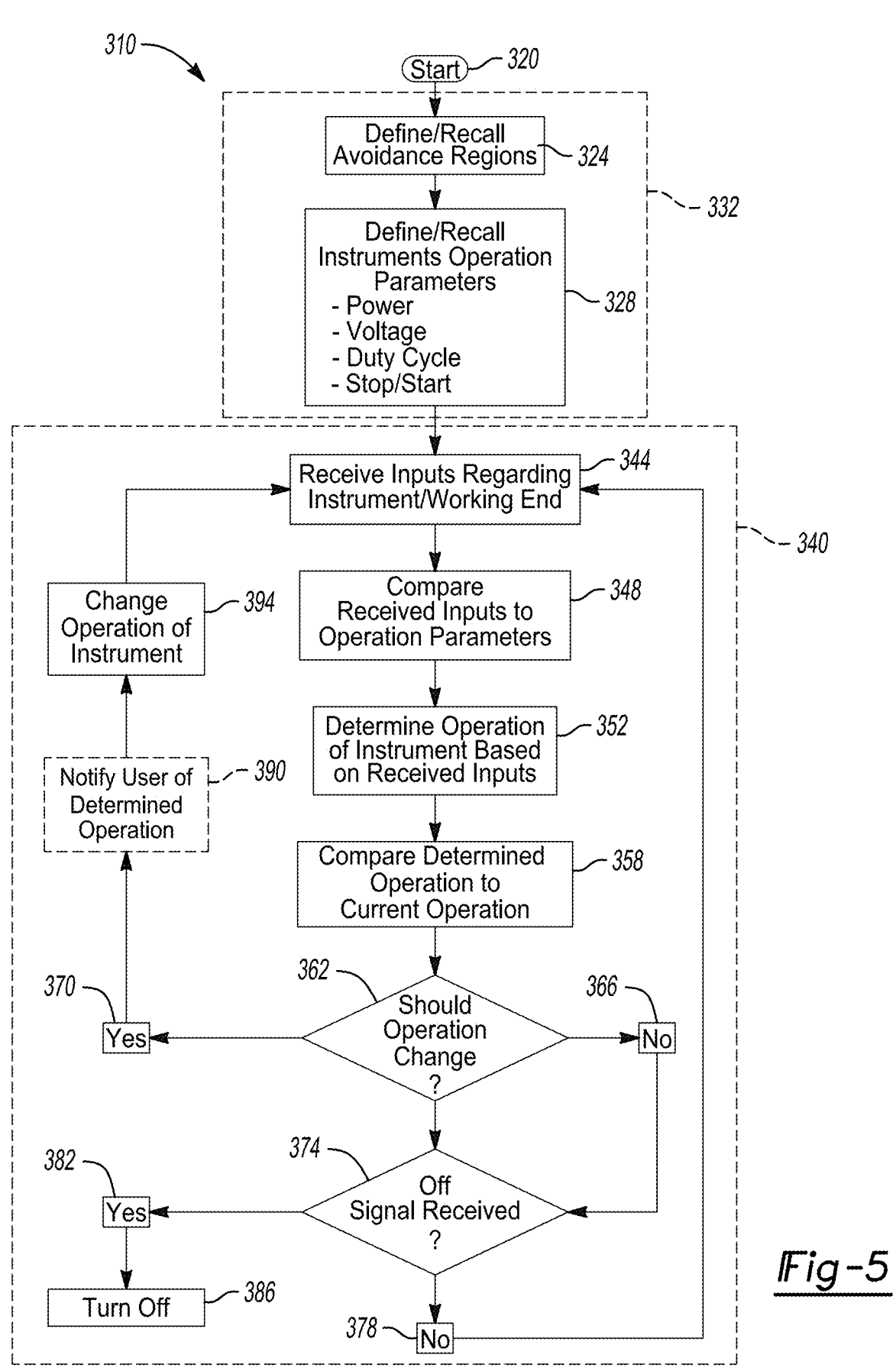
FIG. 5 is a flowchart of an operation of a system, according to various embodiments.

With initial reference to FIG. 5, a process or method 200 is illustrated. The process 200 may be carried out by a processor, such as the processor system 70 and/or processor included in the controller 144. The processor may be designed to carry out specific instructions and/or be a general processor that carries out specific instructions that are saved and recalled from a memory system. Nevertheless, the process 200 may be used to assist in operating the energizable instrument 20 for controlling the working end 32 and/or notifying the user 24, as discussed further herein.

Generally, the process 310 begins at start block 320. The process 310 may then define or recall avoidance regions in block 324. As discussed above, avoidance regions may be those identified by the user 24, recalled according to predetermined restrictions or selections, or other appropriate mechanisms. As discussed above, in various embodiments, the image data and images may be segmented. The user 24 may then identify various portions of the segmented images and/or assist in the segmentation. For example, the user 24 may identify the spinal cord 162 and/or other portions, such as roots or nerves 166 extending therefrom. These portions may be visually identified in the image 120 and/or identified in a navigation space relative to the subject 28.

The definition or recalling of avoidance regions in block 324 may be used to determine operation of the energizable instrument 20, as discussed further herein. The system may also define or recall energizable instrument operation parameters in block 328. The energizable instrument operation parameters may include operation of the energizable instrument 20 and/or the working end 32. In various embodiments, the working end 32 may be provided with a selected power, voltage, have a selected duty cycle, etc.

At block 328, the operation parameters may include various operations of the distal or working end 32 from the generator 144. For example, a voltage may be altered, such as increased or decreased due to the various inputs and operation parameters. Further, a power generated and delivered to the working end 32 may be altered, such as by increasing or decreasing a wattage to the working end 32. In various embodiments, a waveform, such as a duty cycle, may also be altered or selected. For example, a ramp up or ramp down to a peak selected voltage or power may be changed or selected. The waveform may also include changing an on and off signal, such as increase or decreasing a time at a high or peak power voltage relative to a lower or off power voltage. A frequency may also be altered and/or selected. Accordingly, various parameters may be changed that alter the energy at the working end 32 of the energizable instrument 20.

The defining or recalling avoidance spaces in block 324 and the defining or recalling instrument operations in block 328 may be based upon initial operation of the energizable instrument 20 and it may be understood to be a preparation or recalled preparation in block 332. The operation of the energizable instrument 20 may then be carried out by the controller 144, or other selected controller or processor, in operation block or sub-process 340. The operation block 340 may include operation of the energizable instrument 20 according the parameter and receiving inputs to determine which parameters to apply to the operation of the energizable instrument 20 and the working end 32.

In the operation block 340, the controller 144 may receive inputs regarding the energizable instrument 20 and/or working end 32 in block 344. The receiving of inputs may include the inputs from block 200, as discussed above. Accordingly, the inputs may include the predetermined avoidance regions in block 210 that may be recalled in block 324 and/or navigation data in block 70*i*. Regardless the operation of the energizable instrument 20 based upon the inputs received in block 344 may select and/or alter an operation of the energizable instrument 20 when the user 24 has selected to power on or power the energizable instrument 20. Accordingly, the operation in block 340 may be after the user 24 has selected to operate or power the energizable instrument 20.

Based upon the received inputs or after receiving input in block 344, a comparison may be made to the operation parameter input in block 332. The operation parameters may include the avoidance spaces and caution zones, as discussed above, relative thereto in block 324 and the operation of the energizable instrument 20 and/or working end 32 in block 328. The comparison to the received inputs to the operation parameters may be determining whether the working end 32 is near or at an avoidance space, a determination of whether the energizable instrument 20 is at full power, duty cycle, etc. and/or other comparisons. As discussed further herein, for example, the working end 32 may be operated at a full or peak power, voltage, duty cycle at a selected distance from the avoidance spaces and at a second power, voltage, duty cycle at a second distance (e.g., a caution zone) relative to the avoidance spaces. Accordingly, a comparison of the received inputs in block 348 to the operation parameters from block 332 may be made in block 348. After making the comparison in block 348, a determination of operation of the energizable instrument 20 may be made in block 352. As discussed above, the operation of the energizable instrument 20 may be based upon the selected inputs relative or compared to the defined parameters, as discussed above.

After determining an operation of energizable instrument 20 in block 352, a comparison of the determined operation to the current operation is made in block 358. The current operation may be a selected operation of the energizable instrument 20, such generation and delivery of power at a peak power due to a prior input in comparison. In various embodiments, the inputs may be updated or checked at a selected frequency, such as once every second, ten times a second, once every millisecond, or any appropriate rate.

Further, the update rate may change based upon a tracked pose, determined kinematics, etc. of the energizable instrument 20. Nevertheless, the comparison of the determined operation block 352 may be made to the current operation in block 358. The update may include a power signal or other appropriate parameters.

After the comparison in block 358, a determination of whether the operation of the energizable instrument 20 should change in block 362 may be made. In operation, the determination in block 362 may be made by executing selected instructions and/or algorithms. In various embodiments, physics regarding motion and pose of the instrument may be considered and/or machine learning algorithms may be used to integrate the several inputs for making the determination. Navigation data 70i includes both tracking data (e.g., current and recent past energizable instrument 20 poses and orientations) as well as imaging data (e.g. energizable instrument 20 pose with respect to and within subject portions). In one example, navigation data 70i is used to determine kinematics via physics based algorithms, navigation data 70i and avoidance region or space 210 data is used to determine proximities 250 via physics and/or machine learning based algorithms. Further, all of these as well as system parameters 240 may be used to determine energizable instrument 20 parameters via optimization and/or machine learning based algorithms. All these inputs and parameters, therefore, may be used to determine energizable instrument parameters 280 via optimization or machine learning algorithms.

For example, if the comparison in block 358 finds a match between the determined operation and the current operation a determination block 362, no change is determined and a NO path 366 may be followed. If, however, the comparison in block 358 finds that there is not a match between the determined operation and the current operation, a determination in block 362 may be that the operation of the energizable instrument should change and a YES path 370 is followed.

If the NO path 366 is followed, a determination of whether an off signal is received in block 374 may be made. If an off signal is not received (i.e. to stop operation of the energizable instrument 20) a NO path 378 may be followed to again receive inputs in block 344. Thus, the operation of the energizable instrument 20 may be a loop until an off signal is determined to be received at block 374. Accordingly, if an off signal is received in block 374, a YES path 382 may be followed and operation of the energizable instrument may be ceased or it may be turned off in block 386.

As discussed above, the determination block 362 may be that the determined operation does not match the current operation. Thereafter, a YES path 370 may be followed. In following the YES path 370, a notification to the user 24 that the operation of the energizable instrument 20 will change may optionally be made in block 390. The notification of the user 24 that the operation of the energizable instrument 20 will change may be a visual indication, such as displayed on the display screen 84, an audible notification, a haptic or touch sense of feedback, or other appropriate notification. The notification to the user in block 390 may identify or indicate to the user 24 that operation of the energizable instrument 20 will change at a selected time, such as immediately, after a selected period, or the like.

Changing operation of the energizable instrument 20 in block 394 may then follow. As discussed above, the energizable instrument 20 may be operated in a selected or according to a selected operation parameter, such as those recalled in block 328. Accordingly, if a determination is made that the comparison of the determined operation and the current operation does not match, the YES path 370 may lead to changing operation of the instrument in block 394. In various embodiments, as discussed further herein, the change of operation may be from a full power to a second, e.g., lower, power or other change in operation of the energizable instrument 20 in block 394. After changing operation of the energizable instrument in block 394, the operation process 340 may again loop to receive inputs in block 344. It is understood, however, the user may override or provide input to stop the change of operation in block 394. The input may be a selected switch or command (e.g., an audible command) to not accept a change in operation or cease or not allow the change of operation in block 394. For example, after the notify User in block 390, the user may input a cease or stop change command that the NO path 366 is followed rather than to the change operation block 394.

Accordingly, the energizable instrument 20 may be operated according to the process 340 in a substantial loop manner until a signal to turn off the energizable instrument is received. The off signal may be a manual signal from the user 24, such as with a foot switch, hand switch, or other appropriate switch. Other off signals may also include an off signal to cease operation of the energizable instrument 20 after a selected period of time, a selected distance of movement, or the like.

With continuing reference to FIGS. 1-5, and additional reference to FIGS. 6A-6D, according to various embodiments, the energizable instrument 20 with the working end 32 may be operated and moved relative to various portions of the subject 28, such as the disc 34, vertebrae 36, and/or the spinal cord 162. The energizable instrument 20, or any appropriate portion of the energizable instrument 20 may be held by the user 24. It is understood, however, that the energizable instrument 20 may also be held or moved with a selected mechanism, such as a robotic system (e.g., Mazor X Stealth Edition® robotic assisted surgical systems sold by Medtronic, Inc.) that may hold, control, and/or move the energizable instrument 20 in a selected direction.

Figure 6A:
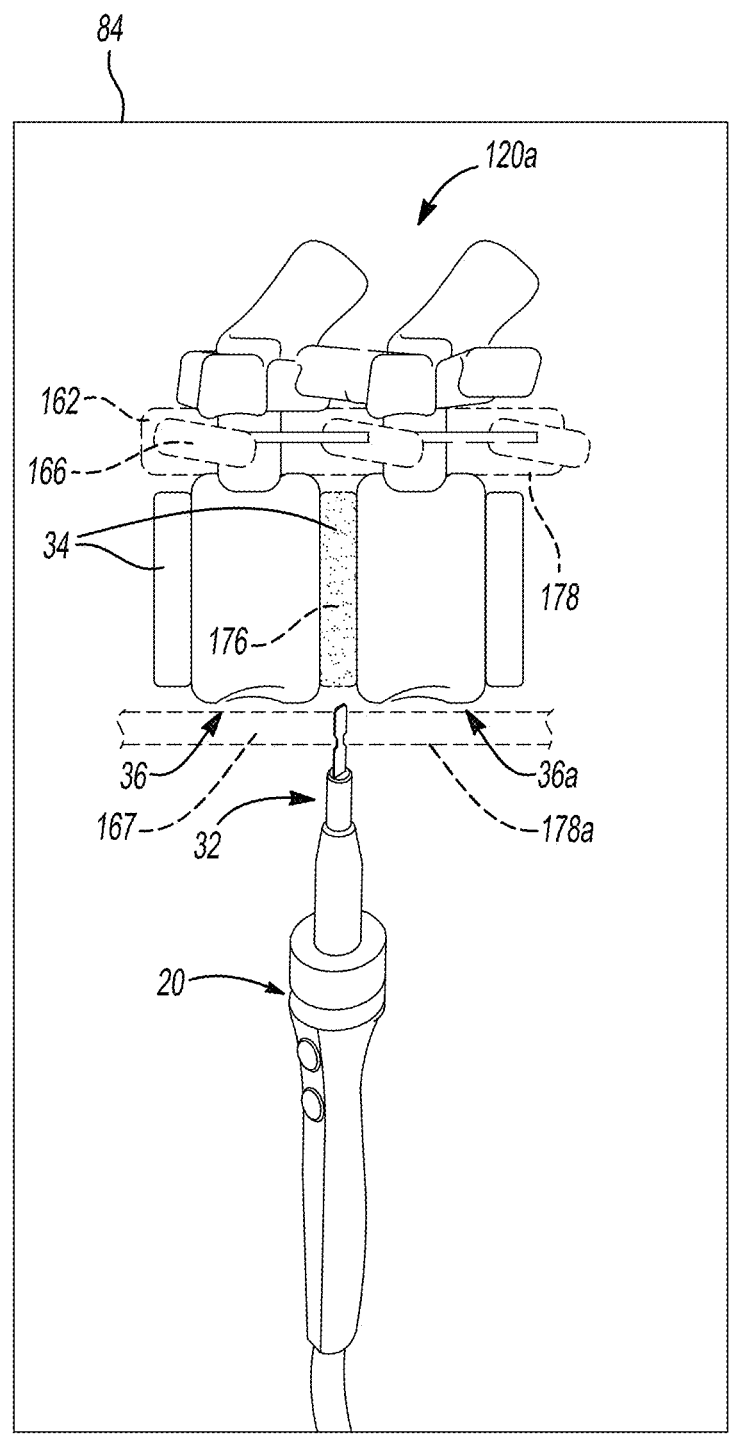

With initial reference to FIG. 6A, the working end 32 may be moved along the planned path 174, as discussed above and illustrated in FIG. 3. The path may or may not be illustrated during the procedure. In such an instance, the working end 32 is being directed toward the disc 34. As discussed above, the image 120 may be used to plan a procedure and the path 174 may be defined for the procedure, which may be stored and/or recalled for display. Accordingly, moving the working end 32 along the path 174 may be a selected parameter for operation of the instrument 20 and the user may be provided with feedback (e.g., visual) that the working end 32 is on the path 174. Power provided to the working end 32 of the energizable instrument 20 may be off or substantially minimal until the working end 32 is near or adjacent to the disc 34. As the instrument moves along the path 174 toward the disc 34 the tracking system, such as the navigation system 33, may be used to determine the navigation data 70i. By the determination of the navigation data 70i, the proximities may be determined in block 250 and the kinematics in block 260. Therefore, the controller 144 may selectively operate, such as with the control signal, the generation of power with the generator to provide the power signal to the working end 32 so that the working end 32 is not energized until the working end 32 is at or adjacent to the disc 34.

The controller 144 may select to or have input, such as based upon the selected operation parameters 240, to provide a maximum or peak power to the working end 32 when the working end 32 is at or in contact with the disc 34, as illustrated in FIG. 6B, when furthest from avoidance regions 178. Maximum power may also be provided when the kinematics of the working end are slow movement, etc. Therefore, the power provided to the working end 32 may be at a selected low or off power until the working end 32 is at or in contact with the disc 34. As the working end 32 moves relative to the disc 34, the navigation system may continuously track and determine a pose of the working end 32 and/or other portions of the energizable instrument 20. Therefore, the navigation data 70i may be updated substantially continuously, or at a selected rate, during a procedure regarding movement of the working end 32. This allows the navigation system 33 to continuously track the pose of the working end 32 relative to the subject 28, such as relative to the disc 34 and other portions of the subject 28, such as the spinal cord or nerves 162, 166.

As discussed above, the working end 32 may be used to remove the disc 34 for selected procedure such as a discectomy. The working end 32 may, however, only or substantially only cut or resect tissue when energized. Thus, when not energized the working end 32 is substantially safe. Therefore, when energized, according to various embodiments, the disc 34 may be removed with the working end 32. The disc 34, once removed, may be replaced with a selected disc implant, or other appropriate procedure, such as the fusion of the vertebrae 36. The disc 34 may be removed according to a selected plan and/or by the user 24 while minimizing removal and/or contact with the working end 32 while it is energized to other tissue or portions.

This allows the working end 32 to be used to remove the disc 34 according to a selected procedure. During the procedure, the navigation system 33 may track the location of the working end 32. As illustrated in FIG. 6B, the working end 32 may be substantially near an outer edge or extent of the disc 34. At the contact location, the controller 144 may energize the energizable instrument 20. While the controller 144 may energize the working end 32 to a selected parameter, such as power, voltage, or duty cycle, the navigation system 33 may further determine navigation data 70i (e.g., pose, kinematics, etc.) during operation of the working end 32 by the controller 144.

Figure 6C:
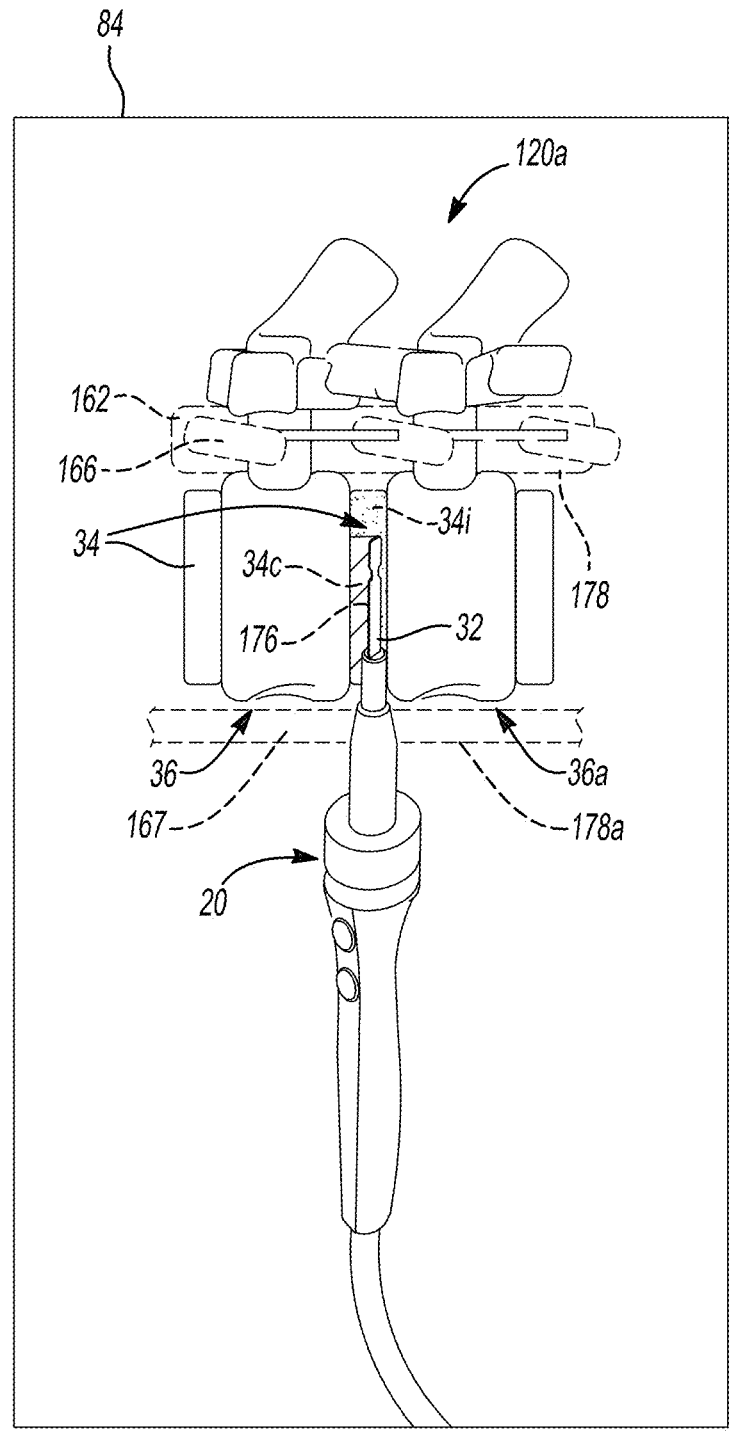

Further, the navigation system 33 may determine poses that the working end has passed, such as by tracking one or more of the tracking devices 40, 40', 40a relative to the subject which may be determined with the subject tracker 98, 98'. The past poses may be illustrated with a cut or removed graphical representation 34c. As discussed above, removal of the disc 34 may be the selected procedure and, therefore, an indication or confirmation of the portion removed may be selected. Accordingly, as illustrated in FIG. 6C, the working end 32 may have passed through an extent of the disc 34. The disc 34 may have a selected change that may be displayed with the display device 84. For example, the disc 34 may include a first color or shading or an initial shading 34i that may be used to indicate an uncut or unremoved area. The removed or cut area may be illustrated with the graphical representation 34c, which may include a color, shading, blink rate, or the like. This allows the user 24 to view the display device 84 and be provided an indication of the area that has been cut 34c and an area that has not been cut 34i. The working end 32 may continue to move through the disc area 34 and cut other portions of the disc 34, which may be further updated with the cut graphical illustration 34c as the disc is cut. Thus, the user 24 may be provided a visual indication, such as with the graphical representation

34i, 34c regarding a cut or removed area of the disc 34 that is represented by an area that is passed with the working end 32.

Further, as illustrated in FIG. 6C, the working end 32 may be nearer the spinal cord 162 and respective nerves 166 as opposed to an initiation of the procedure. As discussed above, the spinal cord 162 and respective nerves 166 may be defined as avoidance regions 178. Further, various caution areas or dimensions may be determined relative to the avoidance spaces 178. As discussed above, the controller 144 may determine operation parameters of the energizable instrument 20 including a power, voltage, duty cycle, or the like.

As the working end 32 continues to move within the subject 28, the pose of the energizable instrument 20 and the working end 32 may be tracked with the navigation system 33 that provides the navigation data 70i as an input for the controller 144. Thus, the controller 144 may continue to control various operation parameters of the energizable instrument 20 during movement relative to the subject 28. For example, as the working end 32 moves closer and/or toward the avoidance spaces 178 the proximities, kinematics, and/or contacts 250, 260, 270, as discussed above, may be determined. Based upon one or more of these, the controller 144 may alter the operation of the working end or generation of power to the working end 32. For example, when the working end 32 or the edge 32e is a selected distance from the avoidance spaces 178, the operation parameters may be changed or altered, such as include reducing power or voltage to the working end 32. Also or alternatively, a duty cycle may be changed to provide less power or energy to the working end 32. Accordingly, as illustrated in FIG. 6C, as the working end 32 moves closer to the avoidance spaces 178 the controller 144 may, according to the process 310 discussed above, alter operation parameters based upon the recalled and/or planned operation parameters in block 328 and may alter them based upon a determination of a planned operation parameters in block 352 as compared to received current operation parameters in block 358.

An alteration of an operation of the energizable instrument 20 may be notified to the user 24, such as by the controller 144 notifying the user in block 284 and the notification of the user in block 390. For example, the notification may include a visual indication (e.g., with the display 84) that the power provided to the working end 32 will be reduced and/or increased. The user 24 may further be provided a haptic feedback, such as with a selected motor within the housing of the energizable instrument 20. Further, as the power is reduced to the working end 32 the ease of cutting may be reduced. Therefore, the user 24 may also be provided a tactile feedback regarding cutting or removing of tissue or other material within the subject 28 as the power is reduced. Thus, the user 24 may be notified, as discussed above.

Figure 6D:
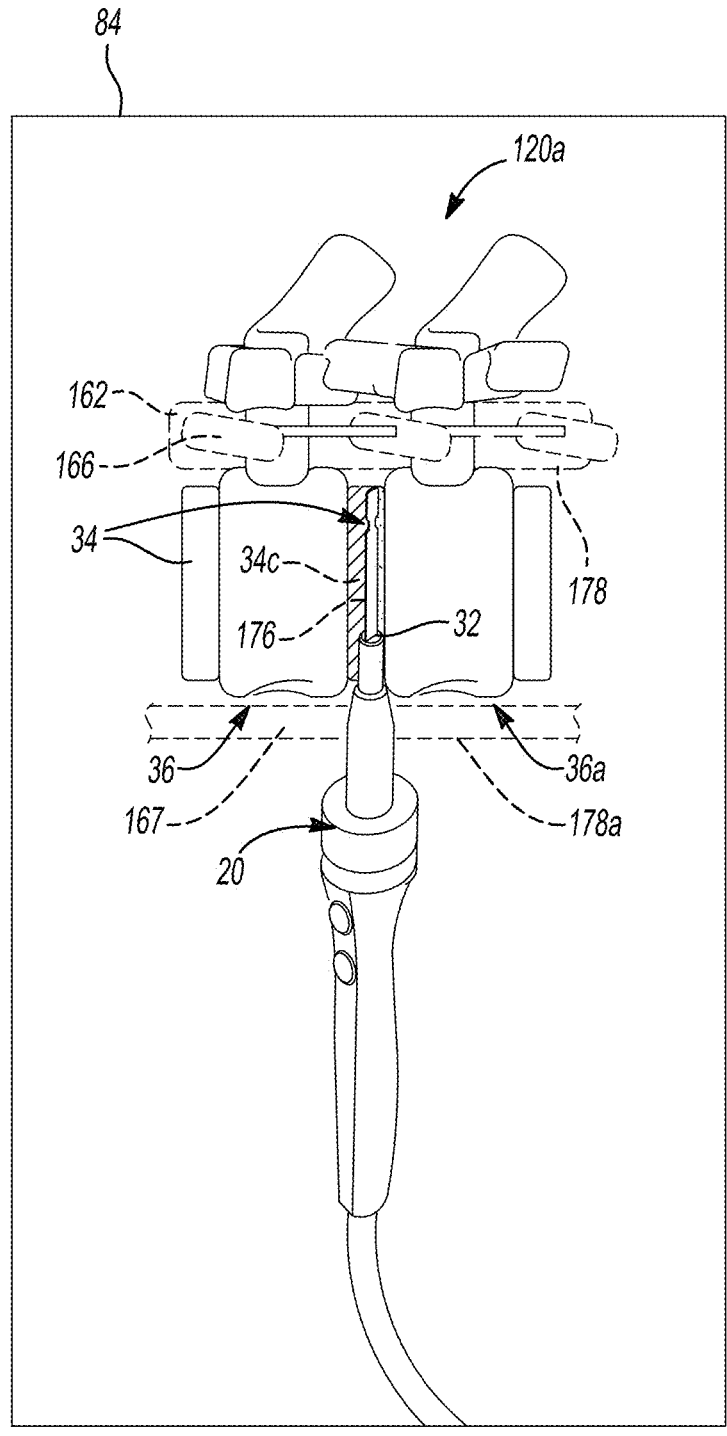

With reference to FIG. 6D, the working end 32 may be moved to remove substantially all and/or all of the disc 34. Therefore, the display screen 84 may illustrate the graphical illustration regarding cutting or removing of the tissue 34c. Further, as illustrated in FIG. 6D, the working end 32 may be positioned substantially at an outer extent of the disc 34 which may be near the avoidance spaces 178 including that of the spinal cord 162. As discussed above, the navigation system 33 may continue to track the pose of the energizable instrument 20 including the working end 32. As the determined pose of the working end 32 may be made as the navigation data 70i, the controller and/or the navigation processor 70 may then determine the proximities 250 and/or other parameters. These may be used to alter operation of the power delivery to the working end 32, and may be used to determine to reduce or eliminate power to the working end 32. Accordingly, based upon the determined pose as a parameter of the working end 32, the instrument the controller 144 may determine to cease power delivery to the working end 32 and a change in operation may be determined in block 362, as discussed above.

By ceasing power delivery to the working end 32 the ability of the working end 32 to cut or remove tissue may be substantially reduced or eliminated. Thus, when the disc 34 is removed a selected amount and/or when the working end 32 is near an avoidance space, the power may be ceased. The cessation of power to the working end may be selected when the working end is within 0.1 millimeters (mm) to about 3 mm form an avoidance space, or other selected distance such as about 0.5 mm or 1 mm to about 2 mm.

Again, notification to the user 24 may be made in an appropriate manner, such as with a visual indication on the display screen 84. Further, as discussed above, the user 24 may be provided tactile feedback regarding the change of power to the working end 32 as the working end 32 may substantially cease to cut tissues as power is removed therefrom. Therefore, cutting of or movement of the working end 32 into the avoidance spaces 178 may be substantially reduced and/or eliminated by reducing and/or selectively ceasing power to the working end 32.

The controller 144 may automatically alter power to the working end 32 based upon a determined pose of the working end 32 relative to various portions of the subject 28, such as determine avoidance spaces that may be determined, as discussed above. The avoidance spaces may be any appropriate portion of the subject and may be determined based upon various inputs. The inputs may be inputs of the user 24, predetermined inputs regarding various portions of the subject and/or portions thereof, or other appropriate determination inputs.

The alteration of power to the working end 32 may be altered according in any appropriate manner, such as that discussed above. The power to the working end 32 may be altered including a change in wattage. The wattage may be altered according to various parameters, such as size or volume of the working end 32, tissue being cut, or other appropriate parameters. Nevertheless the power may be altered from about 0 watts to about 100 watts, including about 60 W to about 90 W. In various embodiments, for example, a peak power may be provided when a maximum distance from the avoidance spaces is determined and/or a selected tissue is to be cut or removed. Further, a duty cycle may be altered regarding the delivery to the working end 32. The duty cycle may be altered to a selected cycle such as about 0.1% to about 100%. The duty cycle may include selected alternating on and off times that may range in seconds, milliseconds, or less and provide duty cycles within the range as noted above. Additionally other parameters may also be altered to alter the operation of the working end 32 such as a voltage display to the working end 32. The voltage again may be reduced or minimal when the working end 32 is tracked at a selected distance and/at the avoidance spaces 178 and maximized when at a selected distance therefrom. The voltage, however, may be about 100 volts (V) to about 5000 V, including selected peak voltages therein.

Example embodiments are provided so that this disclosure will be thorough, and will fully convey the scope to those who are skilled in the art. Numerous specific details are set forth such as examples of specific components, devices, and methods, to provide a thorough understanding of embodiments of the present disclosure. It will be apparent to those skilled in the art that specific details need not be employed, that example embodiments may be embodied in many different forms and that neither should be construed to limit the scope of the disclosure. In some example embodiments, well-known processes, well-known device structures, and well-known technologies are not described in detail.

Instructions may be executed by a processor and may include software, firmware, and/or microcode, and may refer to programs, routines, functions, classes, data structures, and/or objects. The term shared processor circuit encompasses a single processor circuit that executes some or all code from multiple modules. The term group processor circuit encompasses a processor circuit that, in combination with additional processor circuits, executes some or all code from one or more modules. References to multiple processor circuits encompass multiple processor circuits on discrete dies, multiple processor circuits on a single die, multiple cores of a single processor circuit, multiple threads of a single processor circuit, or a combination of the above. The term shared memory circuit encompasses a single memory circuit that stores some or all code from multiple modules. The term group memory circuit encompasses a memory circuit that, in combination with additional memories, stores some or all code from one or more modules.

The apparatuses and methods described in this application may be partially or fully implemented by a special purpose computer created by configuring a general purpose computer to execute one or more particular functions embodied in computer programs. The computer programs include processor-executable instructions that are stored on at least one non-transitory, tangible computer-readable medium. The computer programs may also include or rely on stored data. The computer programs may include a basic input/output system (BIOS) that interacts with hardware of the special purpose computer, device drivers that interact with particular devices of the special purpose computer, one or more operating systems, user applications, background services and applications, etc.

The computer programs may include: (i) assembly code; (ii) object code generated from source code by a compiler; (iii) source code for execution by an interpreter; (iv) source code for compilation and execution by a just-in-time compiler, (v) descriptive text for parsing, such as HTML (hypertext markup language) or XML (extensible markup language), etc. As examples only, source code may be written in C, C++, C#, Objective-C, Haskell, Go, SQL, Lisp, Java®, ASP, Perl, Javascript®, HTML5, Ada, ASP (active server pages), Perl, Scala, Erlang, Ruby, Flash®, Visual Basic®, Lua, or Python®.

Communications may include wireless communications described in the present disclosure can be conducted in full or partial compliance with IEEE standard 802.11-2012, IEEE standard 802.16-2009, and/or IEEE standard 802.20-2008. In various implementations, IEEE 802.11-2012 may be supplemented by draft IEEE standard 802.11ac, draft IEEE standard 802.11ad, and/or draft IEEE standard 802.11ah.

A processor or module or 'controller' may be replaced with the term 'circuit.' The term 'module' may refer to, be part of, or include: an Application Specific Integrated Circuit (ASIC); a digital, analog, or mixed analog/digital discrete circuit; a digital, analog, or mixed analog/digital integrated circuit; a combinational logic circuit; a field programmable gate array (FPGA); a processor circuit (shared, dedicated, or group) that executes code; a memory circuit (shared, dedicated, or group) that stores code executed by the processor circuit; other suitable hardware components that provide the described functionality; or a combination of some or all of the above, such as in a system-on-chip.

The foregoing description of the embodiments has been provided for purposes of illustration and description. It is not intended to be exhaustive or to limit the invention. Individual elements or features of a particular embodiment are generally not limited to that particular embodiment, but, where applicable, are interchangeable and can be used in a selected embodiment, even if not specifically shown or described. The same may also be varied in many ways. Such variations are not to be regarded as a departure from the invention, and all such modifications are intended to be included within the scope of the invention.

What is claimed is:

1. A system to control operation of an energizable electrosurgical RF instrument, comprising:
a controller configured to control a generator configured to generate a power signal to be transmitted to a working end of the energizable electrosurgical RF instrument; and
a processor module configured to execute instructions to:
receive pose data of the energizable electrosurgical RF instrument based on navigation data,
compare a current operation parameter of the energizable electrosurgical RF instrument to a recalled planned operation parameter of the energizable electrosurgical RF instrument;
determine whether the current operation parameter should change based on the comparison; and
if it is determined the current operation parameter should change, generate a control signal to change an operation of the generator to transmit a power signal to the working end of the energizable electrosurgical RF instrument so that an edge portion of the working end of the energizable electrosurgical RF instrument is energized, wherein the recalled planned operation parameter includes a kinematic feature that includes a speed of movement of the energizable electrosurgical RF instrument along a path of the energizable electrosurgical RF instrument.

2. The system of claim 1, wherein the processor module is further configured to execute instructions to:
recall the recalled planned operation parameter,
wherein the recalled planned operation parameter includes at least one of a power, a voltage, a duty cycle, or combinations thereof to be delivered to the working end of the energizable electrosurgical RF instrument, and
wherein the current operation parameter includes at least one of a power, a voltage, a duty cycle, or combinations thereof that is delivered to the working end of the energizable electrosurgical RF instrument.

3. The system of claim 2, wherein the recalled planned operation parameter includes at least one of a planned power, voltage, duty cycle, or combinations thereof at a selected parameter relative to a trajectory path, resection region, and an avoidance region.

4. The system of claim 3, wherein the selected parameter relative to the trajectory path, resection region, and avoidance region includes at least one of a pose feature, a kinematic feature, or combinations thereof.

5. The system of claim 4, wherein the kinematic feature includes at least a rate of change along a path toward the avoidance region.

6. The system of claim 1, further comprising:
an input configured to input a selection of an avoidance region of a subject.

7. The system of claim 6, wherein the avoidance region is at least one of manually determined, automatically determined, or combinations thereof.

8. The system of claim 6, further comprising:
a navigation system configured to track the energizable electrosurgical RF instrument relative to a region of the subject.

9. The system of claim 8, wherein the processor is operable to execute further instructions to determine a past position of the working end of the energizable electrosurgical RF instrument and illustrate relative to a displayed image of the subject the past position of the working end of the energizable electrosurgical RF instrument.

10. The system of claim 1, further comprising:
the generator configured to be controlled by the controller.

11. A method to control operation of an energizable electrosurgical RF instrument, comprising:
determining a pose of the energizable electrosurgical RF instrument having a working end;
generating a power signal to be transmitted to the working end of the energizable electrosurgical RF instrument for performing a procedure; and
executing instructions with a processor module configured to:
compare a current operation parameter of the energizable electrosurgical RF instrument to a recalled planned operation parameter of the energizable electrosurgical RF instrument based on determined pose data;
determine whether the current operation parameter should change based on the comparison;
if it is determined the current operation parameter should change, generate a control signal to transmit an updated power signal to the working end of the energizable electrosurgical RF instrument to change the current operation parameter to an updated operation parameter, wherein the recalled planned operation parameter includes a kinematic feature that includes a speed of movement of the energizable electrosurgical RF instrument along a path of the energizable electrosurgical RF instrument; and
energize an edge portion of the working end of the energizable electrosurgical RF instrument based upon the updated operation parameter.

12. The method of claim 11, further comprising:
executing further instructions with the processor module to determine a planned operation parameter based on a planned pose or path of at least one of the working end of the energizable electrosurgical RF instrument based on the recalled planned operation parameter of the energizable electrosurgical RF instrument.

13. The method of claim 12, further comprising:
executing further instructions with the processor module to receive pose data of the energizable electrosurgical RF instrument based on navigation data, wherein the determined current pose is based on the navigation data.

14. The method of claim 13, further comprising:
determining the pose data with a navigation system;
transmitting the pose data to the processor module; and
coupling a tracker to the energizable electrosurgical RF instrument,
wherein determining the pose data comprises tracking a tracker with a tracking system.

15. The method of claim 14, further comprising:

generating the control signal to transmit the updated power signal to change the current operation parameter to the updated operation parameter by changing at least one of a power, a voltage, a duty cycle, or combinations thereof.

16. The method of claim 14, further comprising:

displaying with a display device an image of a subject and a graphical icon representing a pose of removed portions of the subject based on at least one determined past pose of the energizable electrosurgical RF instrument.

17. The method of claim 11, further comprising:

receiving an input of a determined trajectory path, resection region, and an avoidance region, wherein the recalled planned operation parameter of the energizable electrosurgical RF instrument is based on the input determined trajectory path, resection region, and avoidance region.

18. The method of claim 11, further comprising:

receiving a manual input from a user to cease the updated operation parameter so as to not change the current operation parameter.

19. A system to control operation of an energizable instrument, comprising:

an energizable instrument having a working end;

a generator configured to generate a power signal to be transmitted to the working end of the energizable instrument for performing a procedure; and a processor module configured to execute instructions to:

compare a current operation parameter of the energizable instrument to a recalled planned operation parameter of the energizable instrument based on determined pose data;

determine whether the current operation parameter should change based on the comparison; and if it is determined the current operation parameter should change, generate a control signal to change an operation of the generator to transmit a power signal to the working end of the energizable instrument with an updated operation parameter, wherein the recalled planned operation parameter includes a kinematic feature that includes a speed of movement of the energizable instrument along a path of the energizable instrument.

20. The system of claim 19, further comprising:

a navigation system configured to determine the determined pose data and transmit the determined pose data to the processor module;

wherein the processor module is configured to execute further instructions to:

determine a current pose of at least one of the working end of the energizable instrument based on the determined pose data; and determine a planned operation parameter based on a planned pose of at least one of the working end of the energizable instrument based on the recalled planned operation parameter of the energizable instrument, wherein the navigation system comprises a tracking system and a tracker, and wherein the tracking is coupled to the energizable instrument, and wherein the energizable instrument is an energizable electrosurgical RF instrument.

21. The system of claim 20, further comprising:

a display device configured to display an image of a subject and a graphical icon representing a pose of removed portions of the subject based on at least one determined past position of the energizable electrosurgical RF instrument.

* * * * *